United States Patent [19]

Gibilisco

[11] 4,257,417
[45] Mar. 24, 1981

[54] ADJUSTABLE EYEDROPPER-BOTTLE HOLDER

[75] Inventor: Kenneth J. Gibilisco, Warminster, Pa.

[73] Assignee: Merck & Co., Inc., Rahway, N.J.

[21] Appl. No.: 62,585

[22] Filed: Jul. 31, 1979

[51] Int. Cl.³ .............................................. A61M 1/00
[52] U.S. Cl. .................................................. 128/233
[58] Field of Search ................................ 128/233, 249

[56] References Cited

U.S. PATENT DOCUMENTS

| | | | |
|---|---|---|---|
| 2,722,216 | 11/1955 | Robbins | 128/233 |
| 3,521,636 | 7/1970 | Mahoney et al. | 128/233 |
| 4,183,355 | 1/1980 | Meckler | 128/233 |

Primary Examiner—John D. Yasko
Attorney, Agent, or Firm—Thomas E. Arther; Mario A. Monaco

[57] ABSTRACT

There is provided a bottle holder for a squeeze-type eyedropper bottle which includes a flat spacer member, a bottle holder attached at one end of said spacer member, and a rest piece slidably positioned at a distance intermediate the midpoint and the opposite end of said spacer member.

3 Claims, 5 Drawing Figures

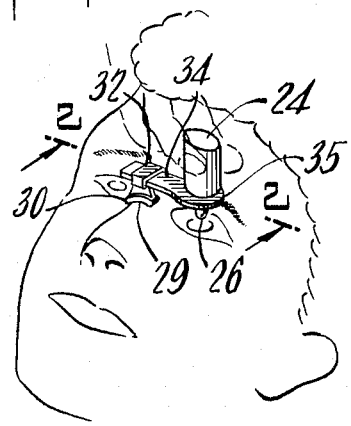
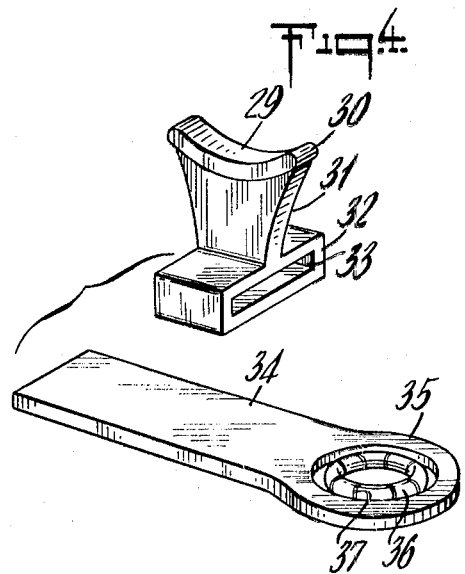
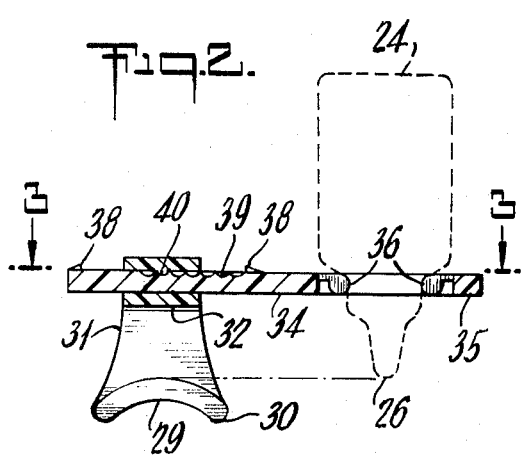
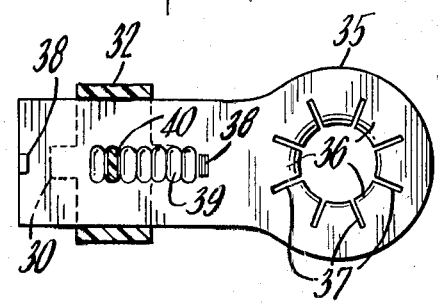
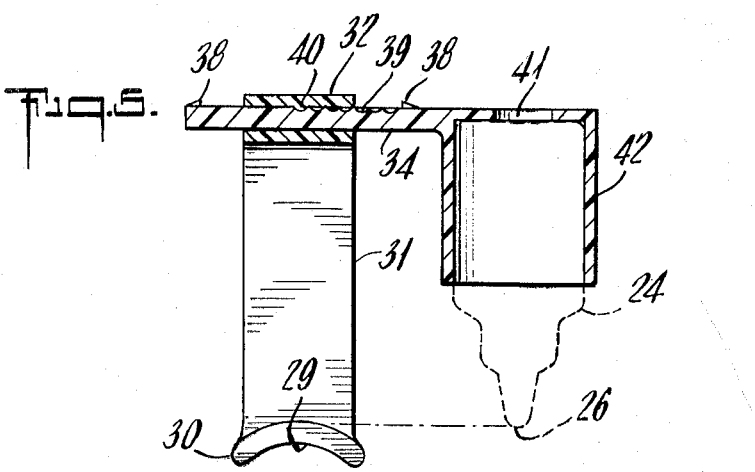

ADJUSTABLE EYEDROPPER-BOTTLE HOLDER

BACKGROUND OF THE INVENTION

This invention is concerned with an eyedropper-bottle holder and stabilizer for administering eyedrops from an ordinary squeeze-type dropper bottle. An object of the invention is the provision of a bottle holder that can be used interchangeably with bottles of different sizes, and that can be adjusted to fit the individual patient, allowing the safe and accurate administration of drops to the eye of the patient.

In the administration of eyedrops, it is important to hold the dispensing tip steady and far enough from the eye to allow the medication to drop directly onto the eyeball and to keep the tips of the dropper bottle from touching the eye. It is important and desirable to drop the medication near the center of the eye, and to do this using only one hand. In self-administration of eyedrops, it is necessary to brace the hand against a steady object and at the same time position the dropper-bottle tip directly over the center of the eye. It is desirable, if possible, to position the tip of the dropping bottle directly over the center of the eye so that the person receiving the medication can see the drop as it forms and falls.

The ordinary eyedropper or the squeeze-type dropping bottle is convenient, simple to operate, and inexpensive to manufacture. However, such devices suffer from the drawback of messiness and unsteadiness of the person who is administering the medication to himself. A number of devices have been prepared to allow steady, safe, and accurate dispensing. Most of these devices suffer from disadvantages such as bulkiness, complicated operation, or high cost of manufacture. In addition, most of the prior art devices suffer from the aspect of being "throw-away" devices. That is, the structure which is intended as a means of assisting the patient is an integral part of the administering device; and thus when the medication is exhausted, the relatively expensive device must be discarded along with the container.

DESCRIPTION OF THE INVENTION

The present invention avoids the difficulties encountered in the prior art devices. One of the prime advantages is that the present device is used with any size and type of eyedropper bottle, and it is used by merely inserting the inexpensive dropper bottle into the holder, adjusting the slidable rest piece, and using it in the manner subsequently described herein. In addition to being an inexpensive and simple device, the present holder is lighter than the devices of the prior art and therefore is much easier to control by the patient providing medication to himself.

Referring now to the drawings, there is described in detail a particular eyedropper-bottle holder useful in dispensing eyedrops in accordance with the present invention.

FIG. 1 is a perspective view showing the eyedropper-bottle holder of FIGS. 2, 3, and 4 in actual use by the patient. ;p FIG. 4 is a perspective view of the two parts of the adjustable eyedropper-bottle holder before assembly.

FIG. 2 is a vertical section view of the assembled eyedropper-bottle holder with an eyedropper bottle positioned ready for use.

FIG. 3 is a horizontal section view of the assembled eyedropper-bottle holder along the plane formed by the underside of the bottle holder arm 34, 35.

FIG. 5 is a vertical section view of an alternate embodiment of the invention illustrating an adjustable holder adapted to hold a specific size bottle.

Referring to FIG. 1, there is shown the preferred embodiment of Applicant's adjustable eyedropper-bottle holder in actual use by the patient. The head of the patient is tilted back and the entire device with dropper-bottle holder inverted with the dropper-bottle tip positioned directly over the pupil of the eye being treated. Before use, the bottle holder is adjusted by sliding the flat spacer bar through the close fitting, rectangularly shaped channel in slide 32 until the horizontal displacement between the depressed center 29 of nose bridge 30 and the dropper-bottle tip 26 matches the horizontal distance between the patient's nose bridge and pupil of the eye being treated.

Referring now to FIG. 4, there are shown the two parts of the adjustable bottle holder before assembly. The entire device is fabricated of a resilient translucent or opaque plastic material such as vinyl or low-density polyethylene, polypropylene, or nylon.

The bottle-holding part as illustrated in FIG. 4 is a flat slide bar member 34 of rectangular cross section having at one end a circular-shaped extension integral with the flat slide member, said extension being provided with an opening adapted to receive the neck of an eyedropper bottle. The opening is provided with a collar 36 of the same material having notches 37 cut through the collar at regular intervals. The collar is designed to provide a snug fit for the neck of dropper bottles of various sizes, thus providing a versatile bottle holder.

The nose bridge piece as illustrated in FIG. 4 comprises a hollow, rectangular slide member 32 having a channel of rectangular cross section 33 adapted to receive slide member 34 in close fitting, slidable relationship. Said slide member carries a vertical, flat spacer bar 31 terminating in a nose bridge having raised ends 30 of concave construction adapted to rest in a stable position on the nose of a patient.

Referring to FIG. 2, there is illustrated in vertical cross section, the method of stabilizing the flat, slide member 34 in one of several positions. The bottom surface of the slide member 34 is provided with means comprising one or more stops 38 to prevent the nosepiece spacer bar 31 from slipping off the end of said slide member or coming into contact with dropper bottle 24. The bottom surface is further provided with spaced, transverse ridges or depressions 39 designed to engage at various stop positions with a raised transverse ridge 40 or the opposing internal surface of the slide channel 33. The vertical spacer bar 31 carrying the nose piece 30 is designed so that the concavity 29 of the nose bridge is slightly less further displaced vertically from the top surface of the flat, slide member 34 than the tip 26 of the dropper bottle 24.

Referring to FIG. 3, which is a horizontal section view, there is illustrated in greater detail the preferred method of holding the slide arm in fixed position in which ridges or depressions 39 engage corresponding depressions or ridges 40 on the opposing, relatively close fitting, bottle-carrying slide member 34. Then is also illustrated the rounded end piece 35 and the integrally attached collar 36 separated by slits 37 to accomodate moderate variations in bottle-neck size in close fitting relationship.

FIG. 5 illustrates in vertical cross section an alternate embodiment of said adjustable eyedropper-bottle holder in which the one end of the bottle-carrying slide member is integrally attached to cylindrically shaped receptacle having a bottom flange 41 extending inwardly from the inner wall of the open-ended, cylindrical shaped receptacle 42. In this embodiment, the length of the vertical spacer bar 31 bearing the nosepiece is adjusted so that the nosepiece concavity 29 is slightly further displaced from the bottle-carrying slide member 34 than the tip 26 of the dropper bottle.

In each of the embodiments, each of the two pieces, the slide member 32 and the spacer bar 34, 35, are molded from a single piece of plastic, preferably nylon or alternatively low-density polyethylene or polypropylene. The present adjustable eyedropper-bottle holder can be modified without departing from the scope of the invention.

What is claimed is:

1. An adjustable eyedropper-bottle holder for use in conjunction with a squeeze-type eyedropper bottle for accurate dispensing of eyedrops, comprising a slidably adjustable nose-bridge rest and a bottle-holding slide bar, said nose-bridge rest being integrally attached to a hollow slide channel by means of a vertical spacer bar, said bottle-holding slide bar shaped to slide in close fitting relationship in said hollow slide channel, and having means at one end to receive and hold an eyedropper bottle.

2. An adjustable bottle holder according to claim 1 wherein said bottle holding and receiving means is an opening circumscribed by a notched resilient collar.

3. An adjustable bottle holder according to claim 2 wherein the opposing surfaces of the slide member are each provided with transverse ridges and opposing depressions as alternate stable stop positions.

* * * * *